US00PP18377P2

(12) United States Plant Patent
Van Zanten

(10) Patent No.: US PP18,377 P2
(45) Date of Patent: Jan. 1, 2008

(54) ***CHRYSANTHEMUM* PLANT NAMED 'GG GOSUN 05'**

(50) Latin Name: *Chrysanthemum morifolium*
Varietal Denomination: GG GOSUN 05

(75) Inventor: Leo Van Zanten, Oxnard, CA (US)

(73) Assignee: G + G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/395,029

(22) Filed: Mar. 31, 2006

(51) Int. Cl.
*A01H 5/00* (2006.01)

(52) U.S. Cl. ..... Plt./295

(58) Field of Classification Search ..... Plt./295
See application file for complete search history.

(56) References Cited

PUBLICATIONS

Brummit, R.K.; "The Garden"; "Chrysanthemum once again," Sep. 1997; pp. 662–663. (2 pages total).*

* cited by examiner

*Primary Examiner*—Kent Bell
*Assistant Examiner*—S. B. McCormick-Ewoldt

(57) ABSTRACT

A new and distinct *Chrysanthemum* plant cultivar is disclosed, characterized by upright daisy type inflorescences with spoon-shape ray florets, consistent flowering response to short days, blooming consistently after 52 days of short day length, yellow ray florets and a moderate branching habit.

1 Drawing Sheet

Latin name of the genus and species: *Chrysanthemum morifolium.*
Variety denomination: 'GG GOSUN 05'.

BACKGROUND OF THE INVENTION

The new cultivar 'GG GOSUN was origination from a cross made by Leo Van Zanten in a planned breeding program in October 2000 between the unpatented male parent 'Tasman' and the female parent 'Red Delano' (U.S. Plant Pat. No. 8,345). The new cultivar was discovered and selected by Leo Van Zanten in June 2001 in Oxnard, Calif.

Asexual reproduction of the new cultivar 'GG GOSUN 05' by vegetative cuttings was performed in Oxnard, Calif., and has shown that the unique features of this new cultivar are stable and reproduced true to type on successive generations.

SUMMARY OF THE INVENTION

The cultivar 'GG GOSUN 05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GOSUN 05.' These characteristics in combination distinguish 'GG GOSUN 05' as a new and distinct *Chrysanthemum* cultivar:

1. Daisy type inflorescence with an upright aspect;
2. Yellow ray florets;
3. Spoon-shape ray florets;
4. And a moderate-branching habit.

Plants of the new cultivar 'GG GOSUN 05' are similar to plants of the male parent variety 'Tasman' in most horticultural characteristics, however plants of the new cultivar 'GG GOSUN 05' have yellow ray florets compared to the white ray florets of the male parent. Also, the new cultivar 'GG GOSUN 05' has more yellow-green foliage than the male parent. Further, the new cultivar 'GG GOSUN 05' has spoon-type ray florets compared to the oblanceolate-shaped ray florets of the male parent.

Plants of the new cultivar 'GG GOSUN 05' are similar to plants of the female parent variety 'Red Delano' in most horticultural characteristics, however plants of the new cultivar 'GG GOSUN 05' have yellow ray florets compared to the dark red ray florets of the female parent. Also, 'Red Delano' has a decorative inflorescence form whereas 'GG GOSUN 05' has a daisy-type inflorescence form. Further, the new variety 'GG GOSUN 05' has spoon-type ray florets compared to the oblong-shaped ray florets of the female parent.

In comparison to the commercially available variety 'Miramar' (U.S. Plant Pat. No. 7,469), 'GG GOSUN 05' has an upright inflorescence aspect compared to the flat aspect of the comparable variety. Additionally, the new variety 'GG GOSUN 05' has a smaller inflorescence diameter. Further, the new variety 'GG GOSUN 05' different color ray and disc florets than the comparable variety.

BRIEF DESCRIPTION OF THE PHOTOGRAPH

The accompanying photograph in FIG. 1 illustrates in full color a typical plant of 'GG GOSUN 05' grown in a 6.5-inch container. Five cuttings were used in the pot, planted late October and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used.

The following observations and measurements describe 'GG GOSUN 05' plants grown in Oxnard, Ventura County, Calif., during the winter months. The growing temperature in the greenhouse ranged from 67° F. and 78° F. Measurements and numerical values represent averages of typical flowering types.

Botanical classification: *Chrysanthemum morifolium* cultivar 'GG GOSUN 05.'
Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 25 cm.
Plant spread: Approximately 30 cm.
Growth rate: Moderate.
Branching characteristics: Moderate branching.
Length of lateral branches: Approximately 20 cm.
Number of leaves per lateral branch: Approximately 20.
Age of plant described: Approximately 104 days.

FOLIAGE

Leaf:
*Arrangement.*—Alternate single.
*Average length.*—Approximately 7 cm.
*Average width.*—Approximately 4.7 cm.
*Shape of blade.*—Ovate.
*Apex.*—Acuminate.
*Base.*—Attenuate.
*Attachment.*—Stalked.
*Margin.*—Pinnately lobed, sinuses between lateral lobes parallel to divergent.
*Texture of top surface.*—Lightly pubescent.
*Texture of bottom surface.*—Lightly pubescent.
*Leaf internode length.*—Approximately 2.2 cm.
*Color.*—Young foliage upper side: Near Yellow-Green 147A. Young foliage under side: Near Green 138A. Mature foliage upper side: Near Green 137A. Mature foliage under side: Near Green 137D.
*Venation.*—Type: Palmately net. Venation color upper side: Near Green 138C. Venation color under side: Near Green 138C.
Petiole:
*Average length.*—Approximately 2.6 cm.
*Color.*—Near Green 138C.
*Diameter.*—Approximately 0.2 cm.

BLOOM

Inflorescence:
*Flowering habit.*—Induced by darkness period greater than 13.5 hours, approximately 52 days of appropriate day length required to induce and develop blooms.
*Inflorescence form.*—Daisy.
*Number of inflorescences per lateral branch.*—Approximately 28.
*Inflorescence diameter.*—Approximately 5 cm.
*Inflorescence depth.*—Approximately 2.5 cm.
*Inflorescence longevity on plant.*—Approximately 35 to 42 days.
*Persistence.*—Persistent.
*Fragrance.*—None detected.
Ray florets:
*Appearance.*—Matte.
*Texture.*—Smooth.
*Average number of ray florets per inflorescence.*—32.
*Number of whorls.*—Approximately 2.
*Shape.*—Spoon.
*Aspect.*—Upright and outwardly spreading.
*Margin.*—Entire.
*Apex.*—Obtuse.
*Length.*—Approximately 2.9 cm.
*Width.*—Approximately 0.8 cm.
*Color.*—Upper surface at first opening: Near Yellow 13A. Upper surface at maturity: Near Yellow 12A. Upper surface at fading: Near Yellow-Orange 15C. Upper surface at first opening: Near Yellow 10B. Under surface at maturity: Near Yellow 10A. Under surface at fading: Near Yellow-Orange 14C.
Disc florets:
*Appearance.*—Matte.
*Texture.*—Smooth.
*Average number of florets per disc.*—Approximately 180.
*Shape.*—Cylindric.
*Apex.*—Obtuse.
*Average length.*—Approximately 0.2 cm.
*Average width.*—Approximately 0.1 cm.
*Color.*—At first opening: Near Green-Yellow 1B. At maturity: Near Yellow-Green 154B. At fading: Near Greyed-Orange 177B.
Peduncle:
*Length.*—At terminal end (shortest): Approximately 3.2 cm. At lateral end (longest): Approximately 6 cm.
*Angle to stem.*—Acute.
*Strength.*—Moderate.
*Color.*—Near Green 137C.
*Habit.*—Upright.
*Diameter.*—Approximately 0.1 cm.
*Surface texture.*—Lightly pubescent.
Inflorescence bud:
*Length.*—Approximately 0.4 cm.
*Diameter.*—Approximately 0.6 cm.
*Form.*—Globular.
*Color.*—Near Green 138C.
Involucral bracts (phyllaries):
*Appearance.*—Matte.
*Texture.*—Lightly pubescent.
*Number.*—Approximately 25.
*Shape.*—Ovate.
*Margin.*—Entire.
*Apex.*—Acute.
*Length.*—Approximately 1 cm.
*Width.*—Approximately 0.4 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 7A.
*Style color.*—Near Yellow-Green 154A.
*Style length.*—Approximately 0.4 cm.
*Stamens.*—Absent.

Disc florets:

*Number of pistils per floret.*—1.
*Stigma shape.*—Cylindric.
*Stigma color.*—Near Yellow 12A.
*Style length.*—Approximately 0.4 cm.
*Style color.*—Near Green-Yellow 1C.
*Number of stamens per floret.*—Approximately 5.
*Anther shape.*—Tubular.
*Anther color.*—Near Yellow 12A.
*Pollen color.*—Near Yellow 12A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG GOSUN 05' as herein illustrated and described.

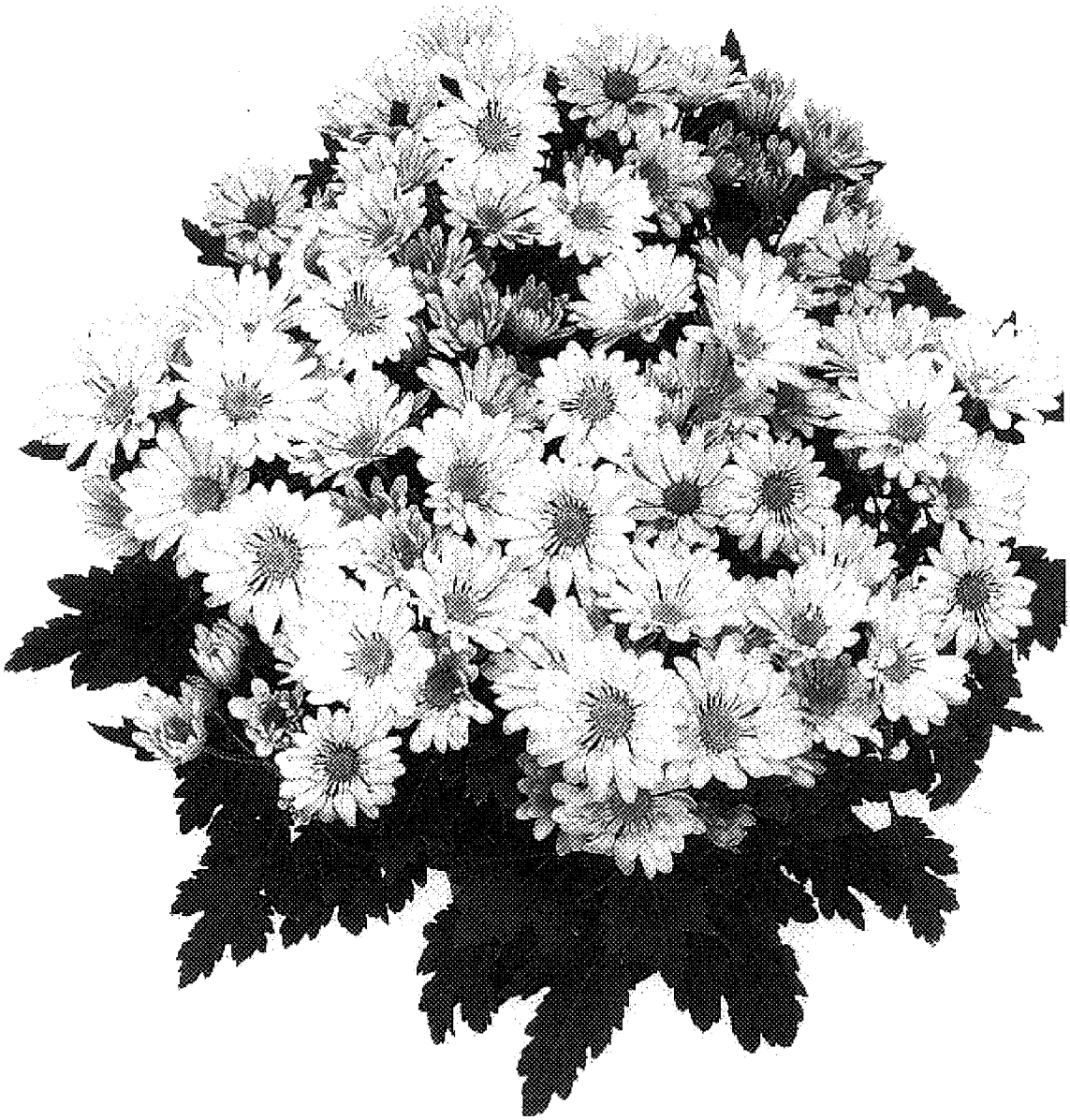

* * * * *